United States Patent
Walker et al.

(10) Patent No.: US 9,835,587 B2
(45) Date of Patent: Dec. 5, 2017

(54) ELECTROPHORESIS RUNNING TANK ASSEMBLY

(71) Applicant: C.C. IMEX, San Diego, CA (US)

(72) Inventors: Winston Glenn Walker, Littleton, CO (US); Richard Chan, La Jolla, CA (US); Rita M. Wong, San Diego, CA (US); Ramey K. Chan, San Diego, CA (US); Po Ling Cheng, San Diego, CA (US)

(73) Assignee: C.C. IMEX, San Diego, CA (US)

( * ) Notice: Subject to any disclaimer, the term of this patent is extended or adjusted under 35 U.S.C. 154(b) by 755 days.

(21) Appl. No.: 14/242,580

(22) Filed: Apr. 1, 2014

(65) Prior Publication Data
US 2015/0276673 A1    Oct. 1, 2015

(51) Int. Cl.
*G01N 27/44* (2006.01)
*G01N 27/447* (2006.01)

(52) U.S. Cl.
CPC . *G01N 27/44721* (2013.01); *G01N 27/44704* (2013.01)

(58) Field of Classification Search
CPC ............. G01N 27/44721; G01N 21/64; G01N 27/44704; G01N 27/44756; G01N 27/44778; G01N 27/44717; G01N 27/44726; G01N 27/44739; G01N 27/44743; G01N 27/44773; C12Q 1/6816; C12Q 2563/173; C12Q 2565/125; C12Q 1/6825; B01D 57/02; B01D 59/42; B01L 2400/0421
See application file for complete search history.

(56) References Cited

U.S. PATENT DOCUMENTS

| | | | |
|---|---|---|---|
| 3,047,489 A * | 7/1962 | Raymond | G01N 27/44756 204/616 |
| 4,520,110 A | 5/1985 | Stryer et al. | |
| 4,542,104 A | 9/1985 | Stryer et al. | |
| 4,603,209 A | 7/1986 | Tsien et al. | |
| 4,657,655 A | 4/1987 | Smoot et al. | |
| 4,714,763 A | 12/1987 | Theodoropulos | |
| 4,774,339 A | 9/1988 | Haugland et al. | |
| 4,786,813 A | 11/1988 | Svanberg et al. | |
| 4,810,636 A | 3/1989 | Corey | |
| 4,812,409 A | 3/1989 | Babb et al. | |
| 4,849,362 A | 7/1989 | DeMarinis et al. | |
| 4,859,582 A | 8/1989 | Stryer et al. | |
| 4,883,867 A | 11/1989 | Lee et al. | |
| 4,908,112 A | 3/1990 | Pace | |

(Continued)

FOREIGN PATENT DOCUMENTS

EP    0965034 B1    5/2007
KR    2020080006479    12/2008

OTHER PUBLICATIONS

Mellichamp et al. (Applied Spectroscopy vol. 13, No. 5, 1959).*

*Primary Examiner* — Sally A Merkling
(74) *Attorney, Agent, or Firm* — John L. Rogitz

(57) ABSTRACT

An electrophoresis running tank assembly uses two opposed rows of LEDs to illuminate DNA-containing gel on a transparent tray positioned between the rows. A respective cylindrical lens is positioned horizontally between each row and a respective edge of the tray. The optical axis of the illumination light is midway between a bottom surface of the gel tray and a top surface of the gel.

28 Claims, 5 Drawing Sheets

(56) References Cited

U.S. PATENT DOCUMENTS

| | | |
|---|---|---|
| 4,945,171 A | 7/1990 | Haugland et al. |
| 4,957,870 A | 9/1990 | Lee et al. |
| 4,981,977 A | 1/1991 | Southwick et al. |
| 5,055,556 A | 10/1991 | Stryer et al. |
| 5,061,336 A | 10/1991 | Soane |
| 5,071,531 A | 12/1991 | Soane |
| 5,132,012 A | 7/1992 | Miura et al. |
| 5,132,432 A | 7/1992 | Haugland et al. |
| 5,135,627 A | 8/1992 | Soane |
| 5,187,288 A | 2/1993 | Kang et al. |
| 5,194,133 A | 3/1993 | Clark et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,275,710 A * | 1/1994 | Gombocz ........ G01N 27/44704 204/461 |
| 5,314,805 A | 5/1994 | Haugland et al. |
| 5,410,030 A | 4/1995 | Yue et al. |
| 5,433,896 A | 7/1995 | Kang et al. |
| 5,436,134 A | 7/1995 | Haugland et al. |
| 5,442,045 A | 8/1995 | Haugland et al. |
| 5,449,446 A | 9/1995 | Verma et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,507,287 A | 4/1996 | Palcic et al. |
| 5,534,416 A | 7/1996 | Millard et al. |
| 5,569,364 A | 10/1996 | Hooper et al. |
| 5,569,587 A | 10/1996 | Waggoner |
| 5,569,766 A | 10/1996 | Waggoner et al. |
| 5,571,410 A | 11/1996 | Swedberg et al. |
| 5,580,990 A | 12/1996 | van den Berg et al. |
| 5,582,702 A | 12/1996 | Cabilly et al. |
| 5,582,977 A | 12/1996 | Yue et al. |
| 5,605,662 A | 2/1997 | Heller et al. |
| 5,606,502 A | 2/1997 | Adachi et al. |
| 5,616,502 A | 4/1997 | Haugland et al. |
| 5,627,027 A | 5/1997 | Waggoner |
| 5,631,337 A | 5/1997 | Sassi et al. |
| 5,647,368 A | 7/1997 | Zeng et al. |
| 5,658,751 A | 8/1997 | Yue et al. |
| 5,696,157 A | 12/1997 | Wang et al. |
| 5,770,365 A | 6/1998 | Lane et al. |
| 5,798,276 A | 8/1998 | Haugland et al. |
| 5,800,690 A | 9/1998 | Chow et al. |
| 5,808,044 A | 9/1998 | Brush et al. |
| 5,824,204 A | 10/1998 | Jerman |
| 5,830,912 A | 11/1998 | Gee et al. |
| 5,846,737 A | 12/1998 | Kang |
| 5,863,753 A | 1/1999 | Haugland et al. |
| 5,865,974 A | 2/1999 | Cabilly et al. |
| 5,877,310 A | 3/1999 | Reddingto et al. |
| 5,929,208 A | 7/1999 | Heller et al. |
| 6,001,229 A | 12/1999 | Ramsey |
| 6,002,003 A | 12/1999 | Shen et al. |
| 6,004,536 A | 12/1999 | Leung et al. |
| 6,008,373 A | 12/1999 | Waggoner et al. |
| 6,008,379 A | 12/1999 | Bensom et al. |
| 6,017,696 A | 1/2000 | Heller |
| 6,043,025 A | 3/2000 | Minden et al. |
| 6,051,380 A | 4/2000 | Sosnowski et al. |
| 6,063,250 A | 5/2000 | Becker |
| 6,127,134 A | 10/2000 | Minden et al. |
| 6,130,094 A | 10/2000 | Waggoner et al. |
| 6,130,101 A | 10/2000 | Mao et al. |
| 6,133,038 A | 10/2000 | Houthoff et al. |
| 6,133,445 A | 10/2000 | Waggoner et al. |
| 6,162,931 A | 12/2000 | Gee et al. |
| 6,198,107 B1 | 3/2001 | Seville |
| 6,210,896 B1 | 4/2001 | Chan |
| 6,238,624 B1 | 5/2001 | Heller et al. |
| 6,245,508 B1 | 6/2001 | Heller et al. |
| 6,258,606 B1 | 7/2001 | Kovacs |
| 6,270,641 B1 | 8/2001 | Griffith et al. |
| 6,284,117 B1 | 9/2001 | Smolko et al. |
| 6,290,909 B1 | 9/2001 | Paul et al. |
| 6,309,601 B1 | 10/2001 | Juncosa et al. |
| 6,315,953 B1 | 11/2001 | Ackley et al. |
| 6,316,608 B1 | 11/2001 | Reynolds et al. |
| 6,339,392 B1 | 1/2002 | Ashihara |
| 6,355,420 B1 | 3/2002 | Chan |
| 6,379,516 B1 | 4/2002 | Cabilly et al. |
| 6,403,311 B1 | 6/2002 | Chan |
| 6,403,367 B1 | 6/2002 | Cheng et al. |
| 6,428,667 B1 | 8/2002 | Glazer et al. |
| 6,472,443 B1 | 10/2002 | Shepodd |
| 6,475,364 B1 | 11/2002 | Dubrow et al. |
| 6,499,499 B2 | 12/2002 | Dantsker et al. |
| 6,512,236 B2 | 1/2003 | Seville |
| 6,518,022 B1 | 2/2003 | Sosnowski et al. |
| 6,551,784 B2 | 4/2003 | Fodor et al. |
| 6,562,632 B1 | 5/2003 | Szalecki et al. |
| 6,567,163 B1 | 5/2003 | Sandstrom |
| 6,569,306 B1 * | 5/2003 | Read ................ G01N 27/44743 204/456 |
| 6,582,660 B1 | 6/2003 | Heller et al. |
| 6,613,525 B2 | 9/2003 | Nelson et al. |
| 6,660,480 B2 | 12/2003 | Ramsey et al. |
| 6,664,047 B1 | 12/2003 | Haugland et al. |
| 6,664,104 B2 | 12/2003 | Pourahmadi et al. |
| 6,716,979 B2 | 4/2004 | Diwu et al. |
| 6,726,880 B1 | 4/2004 | Ackley et al. |
| 6,914,250 B2 | 7/2005 | Seville |
| 6,967,251 B2 | 11/2005 | Haugland et al. |
| 6,974,873 B2 | 12/2005 | Leung et al. |
| 6,977,305 B2 | 12/2005 | Leung et al. |
| 2001/0008212 A1 | 7/2001 | Shepodd et al. |
| 2001/0037940 A1 | 11/2001 | Shih et al. |
| 2001/0052976 A1 | 12/2001 | Juncosa et al. |
| 2002/0004204 A1 | 1/2002 | O'Keefe |
| 2002/0028503 A1 | 3/2002 | Ackley et al. |
| 2002/0058273 A1 | 5/2002 | Shipwash |
| 2002/0064794 A1 | 5/2002 | Leung et al. |
| 2002/0064800 A1 | 5/2002 | Sando et al. |
| 2002/0089658 A1 | 7/2002 | Sevill |
| 2002/0095073 A1 | 7/2002 | Jacobs et al. |
| 2002/0112960 A1 | 8/2002 | Cabilly et al. |
| 2002/0127565 A1 | 9/2002 | Cunningham et al. |
| 2002/0131899 A1 | 9/2002 | Kovacs |
| 2002/0134680 A1 | 9/2002 | Cabilly et al. |
| 2002/0155586 A1 | 10/2002 | Cheng et al. |
| 2002/0164628 A1 | 11/2002 | Kurn |
| 2002/0194909 A1 | 12/2002 | Hasselbrink, Jr. et al. |
| 2003/0027354 A1 | 2/2003 | Geli |
| 2003/0048933 A1 | 3/2003 | Brown et al. |
| 2003/0075491 A1 | 4/2003 | Griffiths |
| 2003/0082604 A1 | 5/2003 | Swanson et al. |
| 2003/0104386 A1 | 6/2003 | Kuhr et al. |
| 2003/0146100 A1 | 8/2003 | Huang et al. |
| 2003/0151735 A1 | 8/2003 | Blumenfeld et al. |
| 2003/0175947 A1 | 9/2003 | Liu et al. |
| 2004/0011650 A1 | 1/2004 | Zenhausern et al. |
| 2004/0052929 A1 | 3/2004 | Kirby et al. |
| 2004/0126279 A1 | 7/2004 | Renzi et al. |
| 2004/0171034 A1 | 9/2004 | Agnew et al. |
| 2005/0074796 A1 | 4/2005 | Yue et al. |
| 2005/0082168 A1 * | 4/2005 | Kang ................ G01N 27/44721 204/456 |
| 2005/0095602 A1 | 5/2005 | West et al. |
| 2005/0121325 A1 | 6/2005 | Updyke et al. |
| 2005/0208534 A1 | 9/2005 | Dallwig et al. |
| 2005/0214810 A1 | 9/2005 | Dallwig et al. |
| 2005/0244976 A1 | 11/2005 | Gee et al. |
| 2006/0141554 A1 | 6/2006 | Gee et al. |
| 2011/0253541 A1 * | 10/2011 | Chan ................ G01N 27/44721 204/612 |
| 2013/0175172 A1 * | 7/2013 | Updyke ........... G01N 27/44778 204/457 |

* cited by examiner

ELECTROPHORESIS RUNNING TANK ASSEMBLY

I. FIELD OF THE INVENTION

This application relates to electrophoresis running tank assemblies.

II. BACKGROUND OF THE INVENTION

The present assignee makes and sells electrophoresis running tank assemblies. An example of an electrophoresis running tank assembly is disclosed in U.S. Pat. No. 6,402,915, incorporated herein by reference.

Electrophoresis running tanks are used to hold a gel containing DNA samples and to place a voltage across the gel. This causes charged DNA particles to migrate across the gel, separating according to size. The ultimate uses of the DNA separation are many.

SUMMARY OF THE INVENTION

As understood herein, existing electrophoresis running tank assemblies and accessories are designed for the commercial and scientific market. As such, they may pose challenges for educational use in, e.g., high schools. For example, while characteristics such as voltages in the 100 volt range and the use of ethidium bromide (EtBr) to stain the DNA for visualization by UV lighting are acceptable in commercial laboratories, higher voltages, EtBr, and UV are not generally desirable in a classroom setting for safety reasons. Additional challenges posed by the classroom setting include the need for relatively compact size for storage, cost, and the need for more than one student at a time to exploit the educational opportunities afforded by a single electrophoresis assembly.

Accordingly, an assembly for electrophoresis includes at least one tank formed with a gel tray platform including a top surface configured for holding at least one gel tray containing gel with DNA therein. At least an anode reservoir is on a first side of the gel tray platform and at least a cathode reservoir is on a second side of the gel tray platform. Both reservoirs are configured for holding buffer during electrophoresis.

If desired, the anode reservoir can be larger than the cathode reservoir. Or, the cathode reservoir can be larger than the anode reservoir.

At least an anode is in the anode reservoir and at least a cathode is in the cathode reservoir.

If desired, a first distance can be established between the anode and a side of the gel tray facing the anode when the gel tray is positioned on the gel tray platform and at least a second distance can be established between the cathode and a side of the gel tray facing the cathode when the gel tray is positioned on the gel tray platform, and the first distance can be greater than the second distance. In other words, the cathode can be closer to the platform than is the anode. In other embodiments the anode may be closer to the platform than is the cathode.

If desired, at least a first source of illumination such as a first group of light emitting diodes (LEDs) can face the platform.

In addition, at least a first lens can be positioned between the first group of LEDs and the platform to focus light from the first group into a pattern defining a first central light axis.

In addition or alternatively, at least a second source of illumination such as a second group of light emitting diodes (LEDs) can face the platform.

In addition, at least a second lens can be positioned between the second group of LEDs and the platform to focus light from the second group into a pattern defining a second central light axis.

In addition or alternatively, the first and second central light axes can be coplanar with each other and can be parallel to and spaced above the top surface of the tray platform.

In some embodiments the anode and cathode are made of carbon such as graphite. The first distance (relating to the anode) can be about twice the second distance (relating to the cathode).

In some implementations the first group of LEDs includes plural LEDs horizontally spaced from each other. The first lens may be an elongated horizontally-oriented cylindrical lens, and the first group of LEDs can be recessed below a surface onto which the first lens is mounted. In examples, the first group of LEDs have flat distal ends through which light emerges. The first wall and the second wall (the walls holding the respective groups of LEDs) can face each other. During operation, a gel tray is positioned on the top surface of the platform, and the first and second central light axes are coplanar with a plane that is located midway between a bottom surface of the tray and a top surface of the gel.

In another aspect, an assembly for electrophoresis includes at least one tank formed with a gel tray platform including a top surface configured for holding at least one gel tray containing gel with DNA therein. At least a first light emitting diode (LED) is juxtaposed with a first wall of the tank facing the platform and at least a first lens is positioned between the first LED and the platform to focus light from the first LED along a light axis that is substantially coplanar with the top surface of the tray. When a gel tray with gel is positioned on the top surface of the platform, the light axis may be coplanar with a plane midway between a bottom surface of the tray and a top surface of the gel.

In another aspect, an electrophoresis running tank assembly includes at least an anode reservoir on a first side of a gel tray platform and at least a cathode reservoir on a second side of the gel tray platform, with both reservoirs configured for holding buffer during electrophoresis. At least an anode is in the anode reservoir and at least a cathode is in the cathode reservoir, with a first distance being established between the anode and a side of the platform facing the anode and at least a second distance being established between the cathode and a side of the platform facing the cathode. The anode reservoir is not the same size as the cathode reservoir, and/or the first distance is not the same as the second distance.

In another aspect, an assembly for electrophoresis that allows an operator to observe the progress of DNA bands as they migrate and separate includes at least a first reservoir for buffer with a cathode element therein, and at least a second reservoir for buffer with an anode element therein. The cathode element and anode element are configured for connection to at least one source of voltage. At least one gel platform is located between the elements and is configured for supporting at least one gel containing DNA therein, stained with a stain to fluoresce. At least a first source of illumination is juxtaposed with a first side of the gel platform and configured for emitting light capable of exciting the stain associated with the DNA. Also, at least a second source of illumination is juxtaposed with a second side of the gel platform and is configured for emitting light capable of exciting the stain associated with the DNA. The second source of illumination is opposite the first source of illumination.

The details of the present application, both as to its structure and operation, can best be understood in reference to the accompanying drawings, in which like reference numerals refer to like parts, and in which:

DETAILED DESCRIPTION

Figure 1:
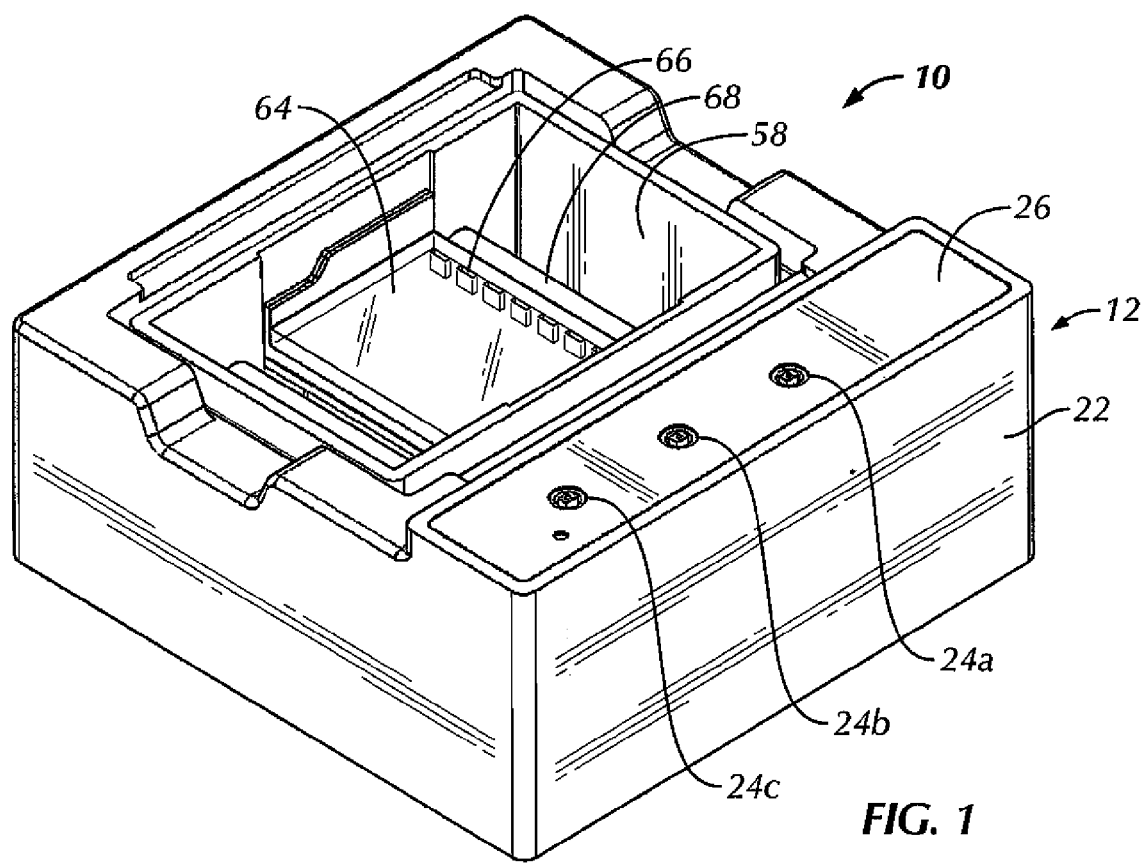
FIG. 1 is a perspective view of an example electrophoresis assembly with the light sub-assemblies not shown.
Figure 1A:
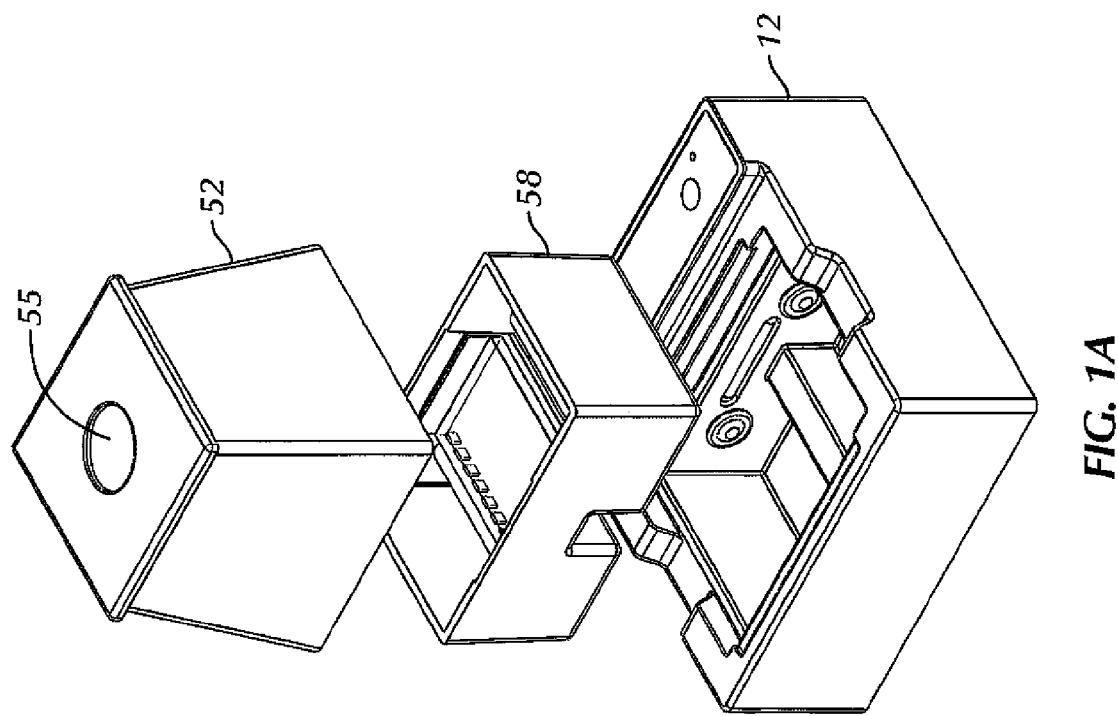
FIG. 1A is an exploded perspective view showing the camera hood, running tank, and housing.
Figure 2:
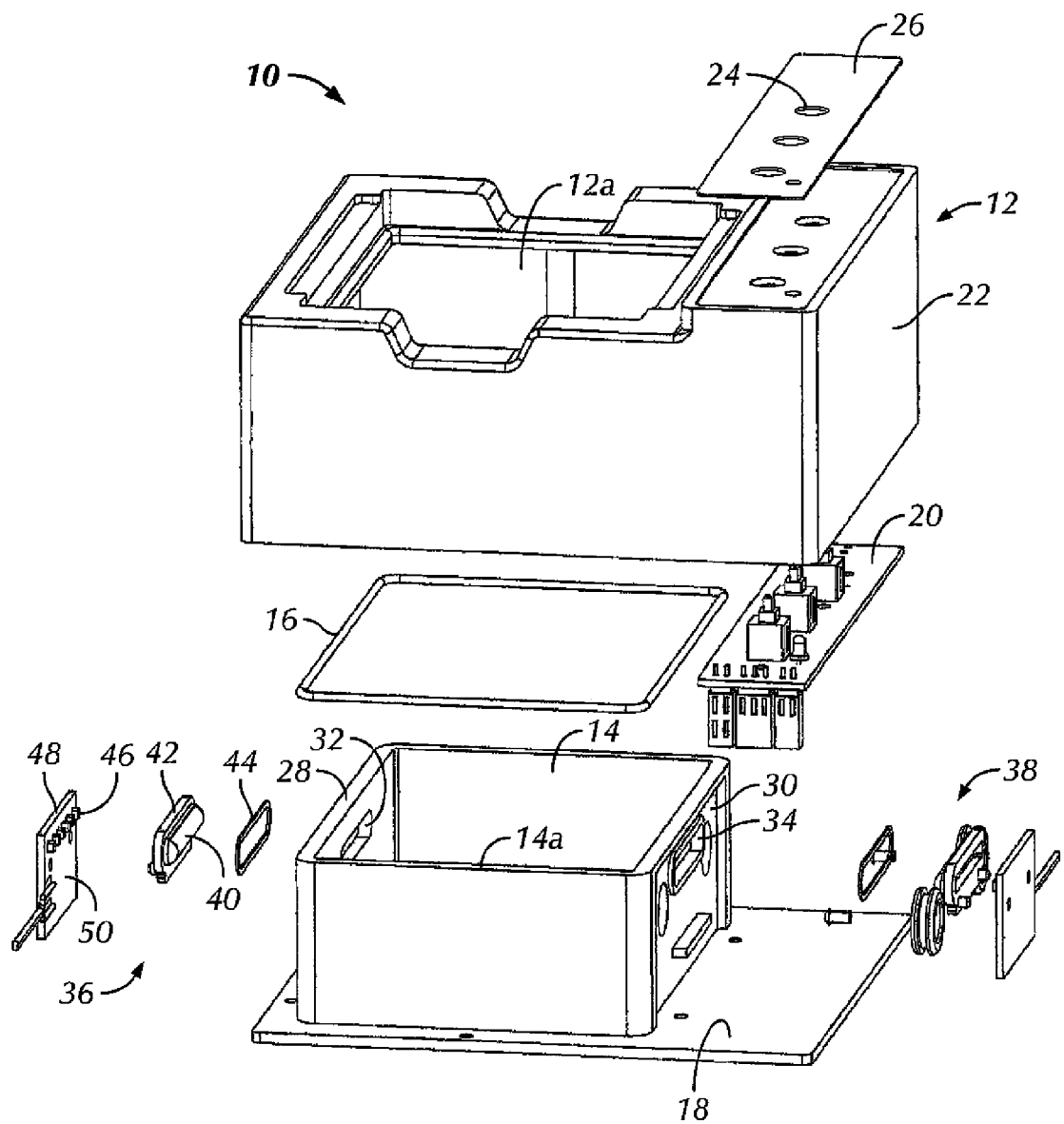
FIG. 2 is an exploded perspective view illustrating certain components of the assembly shown in FIG. 1 without the tank.

Referring initially to FIGS. 1, 1A, and 2, an assembly is shown, generally designated 10, which can be used for conducting electrophoresis, e.g., to separate DNA. As best shown in FIG. 2, the assembly 10 includes an upper housing 12 that can be movably engageable as by sliding engagement with a lower housing 14. The upper housing 12 defines a generally parallelepiped-shaped receptacle 12a for receiving a complementarily-shaped running tank therein.

Both the lower housing 14 and upper housing 12, which can be made of molded plastic, may be generally parallelepiped-shaped structures as shown, with the lower housing 14 being received in a rectilinear opening of the upper housing 12 but not otherwise being visible looking down onto the upper housing 12, as the upper perimeter 14a of the lower housing 14 is received within a complementarily-shaped enclosed top periphery of the upper housing 12. A rectilinear seal 16 may be disposed between the upper housing 12 and a flat plate-like support base 18 on which the lower housing 14 rests and with which the lower housing 14 may be integrally made.

A control panel 20 with electronic components thereon may be received in an instrument compartment 22 of the upper housing 12. The electronic components may include switches that can be operated by manipulating keys 24 on an overlay panel 26 that is positioned onto of the instrument compartment 22, with the keys 24 being appropriately coupled to the electronic components which in turn are coupled as disclosed below to the electrodes and LEDs. As best shown in FIG. 1, the keys 24 may include an electrode key 24a that can be used to energize and deenergize the electrodes described below and a lamp key 24b that can be manipulated to energize and deenergize the LEDs discussed below. If desired, in some examples a high/low key 24c may be provided to toggle between bright and less bright non-zero illumination voltages to be applied to the LEDs, although this key may be eliminated if desired. It will readily be appreciated that this is a simple and intuitive user interface that can easily be understood by students.

As best illustrated in FIG. 2, the lower housing 14 defines left and right opposed side walls 28, 30 that face each other, each being formed with a respective opening 32, 34, racetrack-shaped as shown in some examples, rectilinear in other examples. Substantially identical light sub-assemblies 36, 38 are engaged with each respective opening 32, 34.

Taking the left sub-assembly 36 as an example, it being understood that the following description applies equally to the right sub-assembly, a transparent cylindrical lens 40 that may be integrally formed on a parallelepiped-shaped transparent block 42 is engaged with the left opening 32. The lens 40 may be elongated in the horizontal dimension parallel to the dimension of elongation of the opening 32 to substantially fill the opening 32 to protrude slightly beyond the inner surface of the side wall 28 in an inboard direction as more fully described below. A lens seal 44 established by, e.g., an adhesive may be disposed between the below-described circuit board on the side wall 28 and the block 42 to prevent leakage of buffer through the opening 32 when the sub-assembly 36 is engaged therewith.

Plural, e.g., six, preferably blue light emitting diodes (LEDs) 46 can be arranged in a horizontal row along a metal core printed circuit board 48 with a wide skirt 50 to spread and dissipate heat generated when the LEDs are energized. The PCB 50 may include connections to a power source such as a 42 volt power supply that can be plugged into a wall socket to energize the LEDs 46 and the below-described electrodes, with the key 24b in FIG. 1 being manipulable to open and close the circuit between the LEDs and power supply and with the key 24c in FIG. 1 being manipulable to apply lower and higher voltages to the LEDs through appropriate voltage regulation components within the control panel 20. In some examples, the LEDs 46 have flat distal faces facing inwardly to the lower housing 14 through which light emerges, as opposed to rounded faces. The PCB 48 is mounted against the outer surface of the transparent lens block 42 with the distal faces of the LEDs against the lens block. Accordingly and as will be discussed in greater detail, when the light sub-assembly is installed in the opening 32, the LEDs are recessed radially outward of the inner surface of the side wall 28 with which the lens 40 is engaged.

Figure 3:
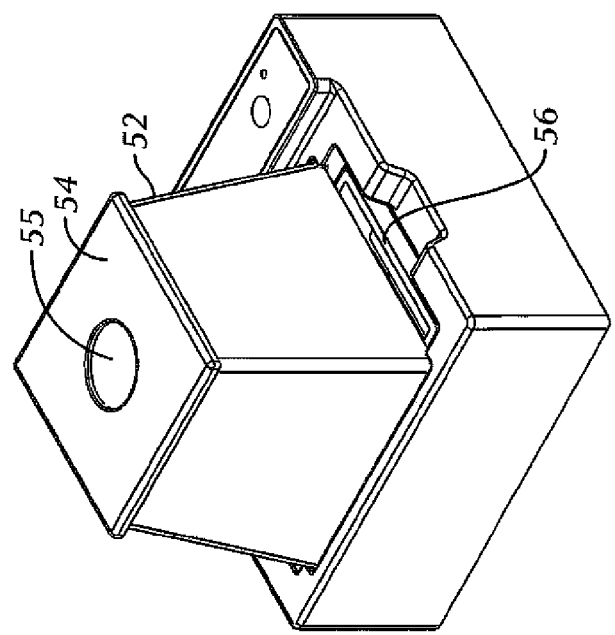
FIG. 3 is a perspective view of the example assembly showing the tinted transparent camera hood installed over the housing.

FIGS. 1A and 3 show that a plastic hood 52 which can be made of amber acrylic with four identical transparent or translucent equilateral trapezoidal sides may be provided, topped by a square, also of amber acrylic. The four sides advantageously provide filters to allow up to four people to simultaneously observe the DNA bands while they are migrating. The top square part can be covered by an opaque, e.g., black, camera mount 54 with a transparent or translucent amber-colored aperture 55 as shown for a camera to image through. The underlying amber acrylic on the top square provides a filter for the camera. Thus, the images taken by the camera are not affected by distortions from perspective, as they would be if taken from the side. The hood surfaces are spaced far enough from the gel that condensation does not occur. Indeed, the hood is sized such that lateral apertures 56 (FIG. 3) extend laterally beyond the sides of the hood are established between the hood-tank interface so that excess condensation from the running tank can vent off without unduly condensing on the hood.

Figure 4:
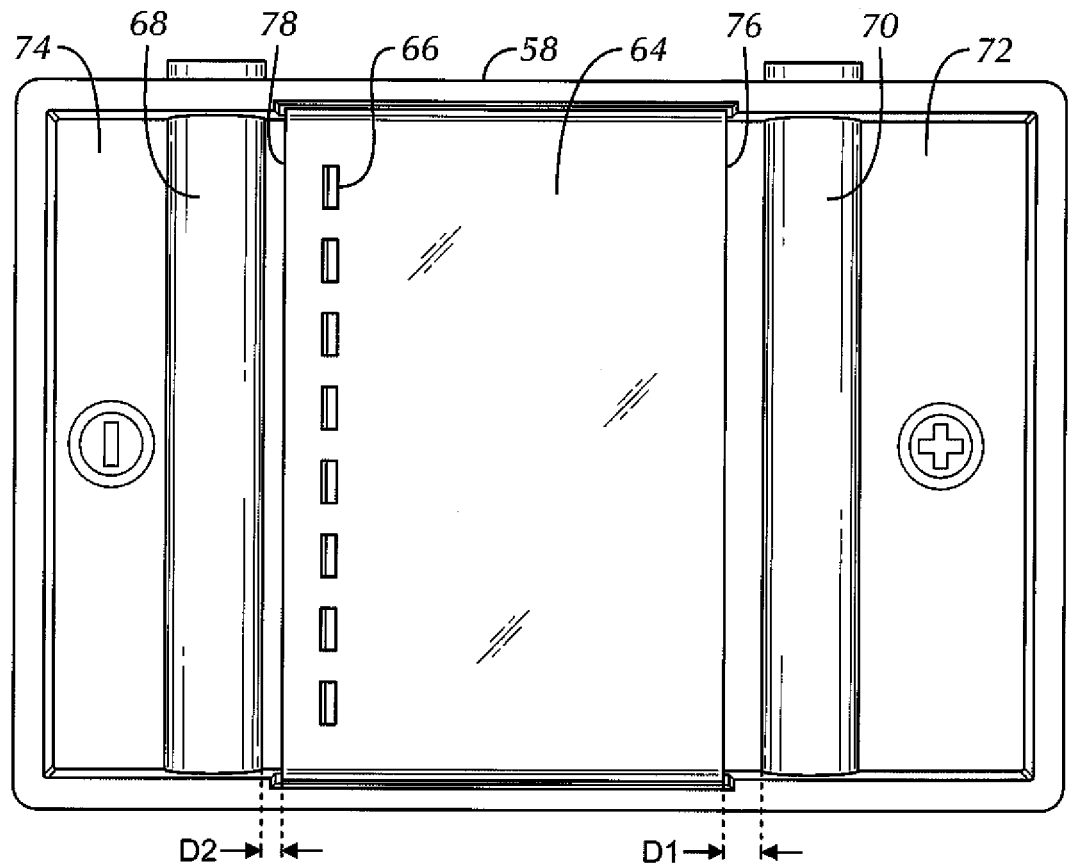
FIG. 4 is a top plan view of the example running tank.
Figure 5:
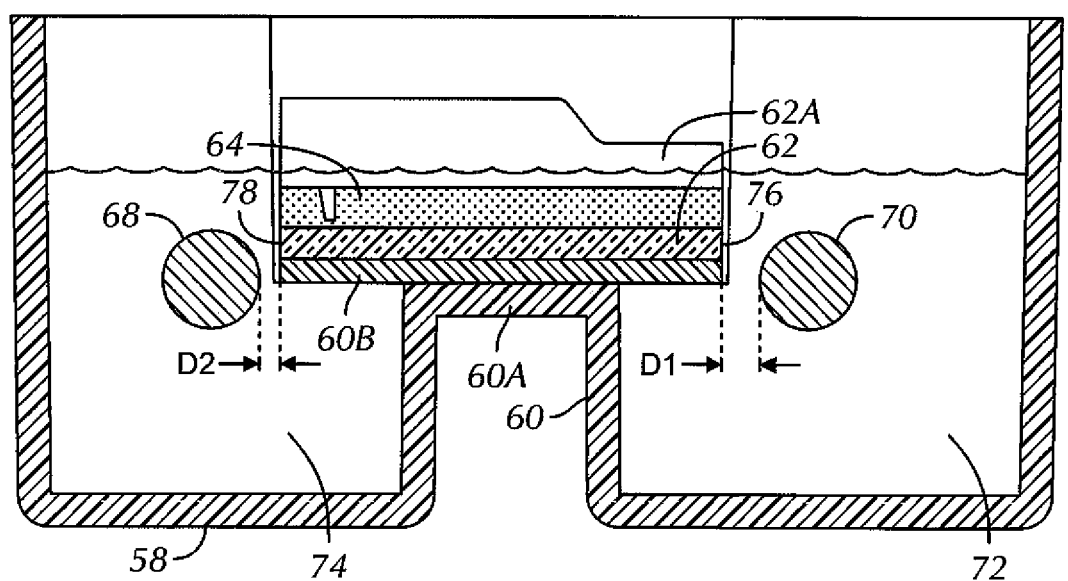
FIG. 5 is a side elevation view of the example assembly without the optical components.

Cross-referencing FIGS. 1, 1A, 4, and 5, a transparent, in some embodiments polycarbonate running tank 58 may be slidably disposed in (by hand) and removed from (by hand) the receptacle 12a in the upper housing 12. FIG. 5 best shows that the running tank 58 may be integrally formed with an opaque, preferably dark or black (for viewing) gel tray platform 60. In some embodiments the portions of the platform 60 below the DNA sample wells (when the gel tray is placed on the platform) may be roughened to facilitate identifying which way the gel tray should be placed on the platform and also to offer a contrast to wells 66 in the gel. The platform 60 may be a hollow parallelepiped-shaped structure as shown with a specular top surface 60A configured for holding a transparent, in some embodiments acrylic/polycarbonate, gel tray 62 containing gel 64 with DNA therein. Typically, samples with DNA in them are loaded into wells 66 (FIGS. 1 and 4) that are formed as shown in a row along an edge of the gel that typically faces a cathode 68, with the opposite edge of the gel facing an anode 70. The cathode 68 and anode 70 may extend through respective openings in the tank 58 to wipe against electrical contacts on the inside wall of the upper housing 12 to provide an electrical path to energize the electrodes using the above-mentioned 42 volt example power supply. In an example, both the anode and cathode are made of carbon of, e.g., graphite with a density of 1.85 for economy, it being understood that other materials may be used.

It may be appreciated in reference to FIG. 1 and will be described in greater detail below that the gel tray 62 has a clear bottom wall defining a bottom surface that rests on the gel support platform 60 when a person positions the gel tray 62 onto the top surface 60A of the platform 60 as shown in FIG. 5. The bottom wall of the gel tray 62, which supports the gel 64 and which defines a top gel surface, is positioned on the top surface of the platform. When the tray with gel is on the platform, the side edges of the gel, tray, and platform may be flush with each other as shown in FIG. 5.

With particular reference to FIGS. 4 and 5, in the example shown, a first buffer reservoir 72 is located on a first side of the gel tray platform 60 and a cathode reservoir 74 is located on a second side of the gel tray platform, with both reservoirs 72, 74 being configured for holding buffer during electrophoresis. In the example shown, the anode reservoir 72 is the reservoir in which the anode 70 is disposed, and as can be appreciated in reference to FIGS. 4 and 5 the anode reservoir 72 is larger than the cathode reservoir 74, in which the cathode 68 is disposed.

As also shown in FIGS. 4 and 5, in example implementations a first perpendicular distance D1 is established between an inboard tangent of the anode 70 and the side 76 of the gel tray facing the anode 70. On the other hand, a second perpendicular distance D2 is established between an inboard tangent of the cathode 68 and the side 78 of the gel tray facing the cathode, and the first distance D1 may be greater than the second distance D2 and in some embodiments may be twice D2.

As understood herein, using a larger anode reservoir and greater distance between the gel and the anode as compared to the distance between the gel and the cathode, ion depletion in the buffer advantageously may be reduced to promote electrophoresis. The anode and cathode may be different sizes from each other or the same size, e.g., 9.53 mm diameter electrodes.

Because the running tank 58 is insertable and removable by hand with the upper housing 12 and contains only the electrodes 68, 70, with the remaining electronic components being contained in the housing 12/14, the running tank 58 can be easily removed from the housing and cleaned as needed without requiring any electrical disconnections and without exposing the housing, where the electronics are, to cleansers for the running tank.

Figure 6:
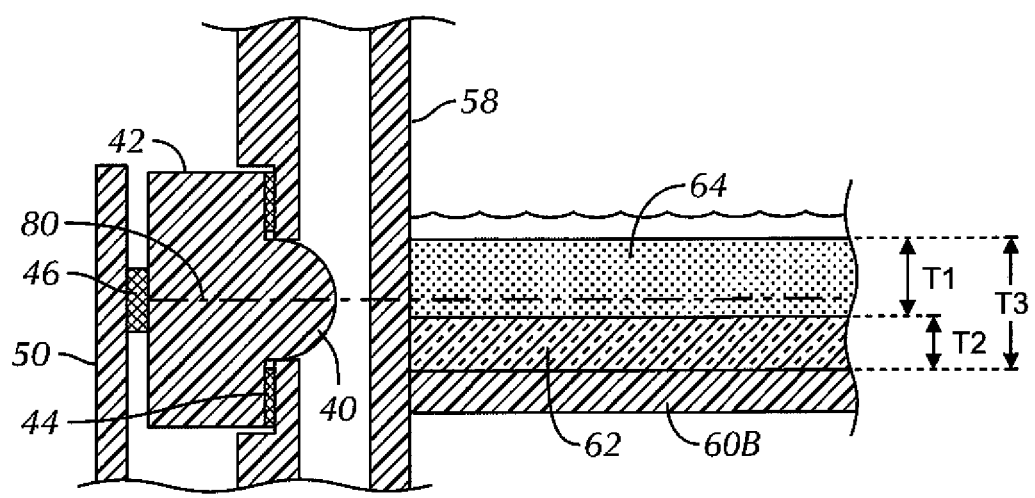
FIG. 6 is a schematic partial side elevation view of the example assembly showing an embodiment of the optical components.

Referring now to FIGS. 5 and 6, the gel tray platform 60 may have a top horizontal flange 60A and on top of that a shelf platform 60B, the top surface of which, except for the above-described roughened well sectors, may be speculative and opaque, preferably dark or black for better viewing of DNA migration during electrophoresis. The bottom wall of the typically transparent gel tray 62 rests on the shelf 60B when a person has established a DNA-bearing gel in the tray. The tray 62 may include vertical plate-like sides 62A rising from the left and right edges of the bottom wall of the gel tray as shown but vertical sides may not be provided on the front and back edges of the bottom wall of the gel tray 62.

In the non-limiting example shown, the gel 64 may be 4 mm thick, the bottom wall of the gel tray may be 3 mm thick, and the shelf 60b may be 2 mm thick. The above-described example larger anode 70 reservoir and greater anode-to-gel distance as compared to the cathode side may also be discerned in FIG. 5.

FIG. 6 illustrates the optical axis 80 of light from the LEDs exiting the lens 40 of the left light sub-assembly 36. Recall that the right light sub-assembly 38 with preferably the same optical axis also illuminates the gel from the opposite, or right, side of the gel in some embodiments. Thus, the light axes of the light sub-assemblies can be coplanar with each other.

As shown best in FIG. 6, the light axis 80 also preferably is co-planar with a plane that is midway between the top surface of the gel 64 and the bottom surface of the gel tray 62. Thus, if the thickness of the gel is T1 and the thickness of the tray is T2, with the total thickness of the tray plus gel being T3, the optical axis 80 is located ½T3 above the bottom surface of the tray 62. Using the example thicknesses shown in FIGS. 5 and 6, the optical axis 80 would be 3.5 mm above the bottom surface of the tray, i.e., in this example, just above the top surface of the tray.

As understood herein, a gel commonly used in electrophoresis is agarose, and while it is crystal clear when heated in an aqueous medium, it becomes somewhat cloudy when it solidifies. Thus, the lanes at the edge of the gel show the DNA bands more clearly than those toward the center of the gel. To overcome this imbalance, the tray 62 has a relatively thick base (e.g., greater than 1.5 mm) to establish a light pipe to carry some LED illumination toward the center of the gel, with some LED illumination (above the axis 80) directly illuminating the gel from the incident edge of the gel. Since the tray is on the opaque shelf 60B on which it rests, any light reaching the lower surface of the tray is reflected by the specular top surface 60A. However, light reaching the upper surface of the tray is allowed to escape into the gel since the index of refraction of the gel is nearly equal to the acrylic. Any light reaching the far wall is somewhat reflected to give it a second chance to try to escape into the gel.

Figure 7:
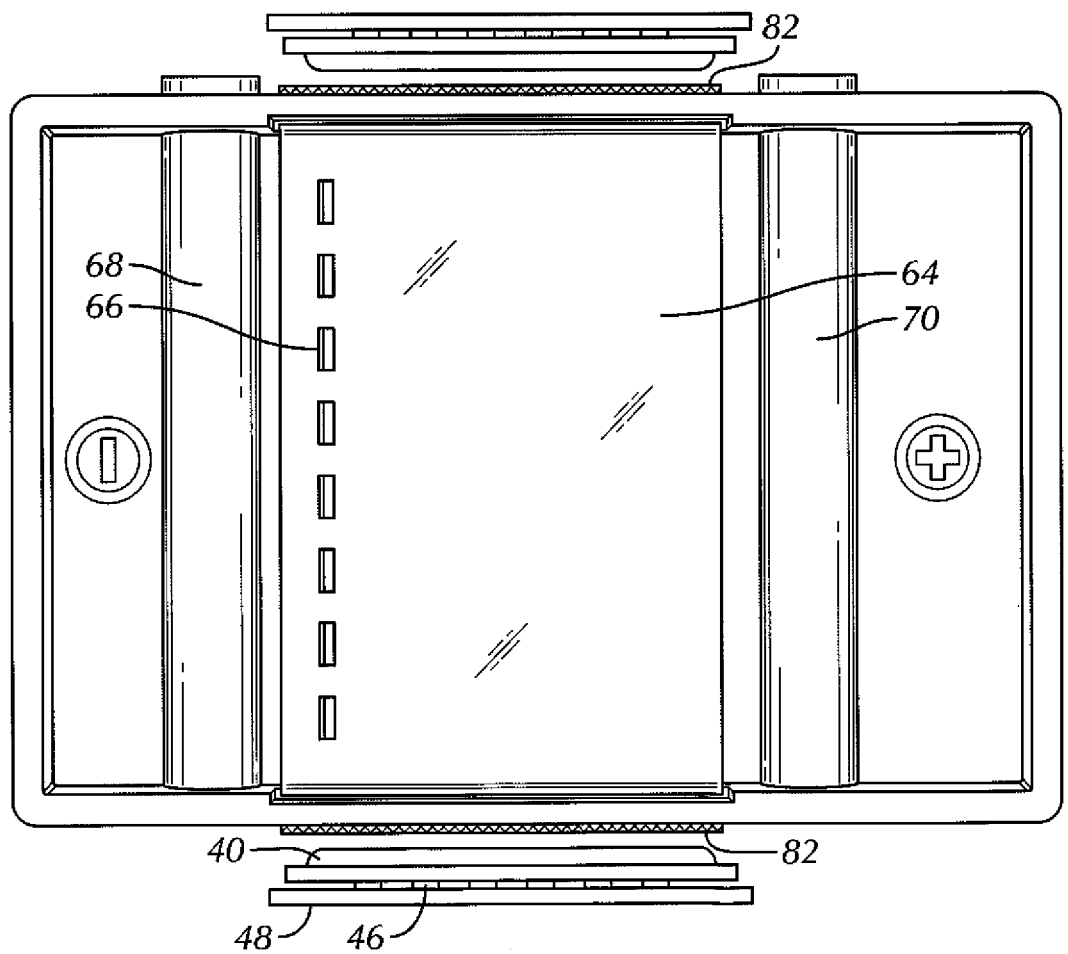
FIG. 7 is plan view of an embodiment showing a DNA migration path orthogonal to the direction of illumination.

As shown in FIG. 7, because some of the light is not reflected, but escapes and is lost, this loss can be substantially eliminated by placing a one-way dielectric filter 82, either by deposition or as a separate component, on or near the outside wall of the tank. As also can be appreciated in reference to FIG. 7, since the DNA migrates in a line between the cathode and anode, the light sources are positioned to illuminate the DNA along a light axis that is orthogonal to the direction of migration of the DNA, with the light sources disposed adjacent the gel tray platform between the electrode reservoirs.

In other embodiments, the lens 40 may not protrude through the housing wall 28 as shown in FIG. 6. Instead, it may be a cylindrical semi-circular lens located completely behind the wall 28, in which case the wall 28 should be transparent, with the LEDs 46 located in turn behind the lens.

To provide adequate migration of the DNA in the time allocated to running a gel experiment at a low, safe voltage, carbon is used as the electrode material. The density of the carbon when embodied as graphite may be 1.85. The electrodes may have lengths between 3.2 mm to 12.7 mm. The electrodes may be positioned as described above to maximize the voltage drop across the gel by minimizing the voltage drop from the electrodes to the gel edges. This undesirable voltage drop derives from three factors. First is the electrode surface to buffer resistance. This can be minimized in example embodiments by using relatively large electrodes. Second is the voltage drop within the buffer itself. This can be minimized in example embodiments by using buffer with greater conductivity in the reservoir than the buffer within the gel, and by minimizing the length of the electrical path from the electrode to the gel edge. Third is the voltage drop immediately adjacent to the gel edge. Nucleic acid migration depends on a copious supply of ions at this interface, and can be minimized in example embodiments by locating the electrode away from the gel edge, allowing buffer to circulate freely in this region.

As understood herein, the desires of the second and third factors are in conflict, requiring a compromise in electrode position, both horizontally and vertically. The optimum location for an example embodiment is with the top of the electrode covered by 4.5 to 5 mm of buffer, and moved away from the gel edge for the cathode and for the anode. Other embodiments may require different spacing since these distances are dependent on voltage, buffer conductivity, reservoir size and shape, and gel thickness and length. Preferably, relative electrode position height in the assembly is established such that the top of the electrode is tangent to the bottom of the gel as shown in FIG. 5, so that the electrode is covered by buffer the thickness of the gel, plus the depth of the buffer covering the gel. Moreover, as described above the lateral distance of the anode from the gel may be about twice that of the cathode. In one example, the distance from the vertical tangent of the anode to the edge of the gel facing the anode may be 4 mm whereas the distance from the vertical tangent of the cathode to the edge of the gel facing the cathode may be 2 mm.

With respect to the interior structure of the assembly, to get more buffer in the vicinity of the gel-electrode for less ion depletion in the buffer (leading to a better DNA migration rate), the interior walls of the reservoir in example embodiments are relatively close together such that a thin opaque (preferably dark-colored) shelf the width of the gel tray is placed on a narrow platform between the reservoirs to support and stabilize the gel tray as described above.

With respect to reservoir size, a smaller size is desired both to facilitate storage and minimize the amount of buffer needed in the reservoirs, with the reservoir in which the anode is disposed preferably being larger than the reservoir in which the cathode is disposed.

As mentioned above, to best observe the fluorescence of the stain binding to the DNA molecules, a dark background is desirable, and so a dark, preferably black, shelf 60B is used to support the gel tray 62. Moreover, to assist in loading specimens into the wells of the gel, it is desirable to have a non-reflective background under the wells. To this end, as mentioned above a roughened region may be established on the shelf 60B under the well locations, which also helps the student orient the gel tray so the wells are toward the cathode.

With respect to buffer composition, TAE (Tris base, Acetic acid and EDTA), TBE (Tris base, Boric acid and EDTA), SA (Sodium Acetate) and SB (Sodium Borate) can be used as examples. With respect to buffer concentration, a higher buffer concentration in the reservoir than in the gel can increase the rate of electrophoresis. Therefore, a concentration ratio of two to one between the reservoir and gel can be used as example. To establish a gel, agarose or agar-agar may be used.

With respect to types of DNA stains that may be used, SYBR Safe, SYBR Gold, SYBR Green and GelGreen may be used, with GelGreen providing the best combination of shelf life, performance and price. GelGreen fluorescence has a peak response to blue light of about 498 nm, and emits at about 525 nm. If it is not desired to use a dielectric filter to separate the two wavelengths, the center excitation wavelength of the LEDs may be established to be 472 nm to produce adequate fluorescence. Because the skirt of emission has virtually vanished at 525 nm, a filter of transparent amber acrylic provides an economical and very effective filter.

In applying the stain to the substance that is to be made into the gel, the DNA specimen many be stained, or the stain may be placed in the gel, so that the stain is present during the run, or the gel may be stained after the run. Putting the stain in the gel prior to run is preferred.

In addition to the above, a casting stand may be provided that is capable of holding two trays, and also capable of positioning two combs. Also, at least one gel comb capable of creating wells in two trays may be supplied. One edge has eight teeth at the location of each of the two trays, while the other edge has six somewhat larger teeth, similarly positioned. The teeth can be wedge shaped, with a vertical surface oriented toward the anode. This shape confers several advantages, including the ability to have a larger loading volume, while maintaining band sharpness, and keeps the well openings from collapsing. As soon as an electric field is applied, the negatively charged DNA move quickly to the vertical surface, and distribute uniformly. A casting stand cover may be provided along with a detachable power source in the form of a 42V AC adapter to power the electrodes.

In some implementations, the sides of the tank may be recessed at the exact location of the shelf to fit and align the tray to its correct location relative to the electrodes.

With the above in mind, it may now be appreciated that present principles enable students to experience and conduct the process of electrophoresis while enabling simultaneous use of a single low-cost assembly by multiple students without the use of chemicals or lighting of concern. Students can observe the bands of DNA molecules as they migrate from the wells adjacent to the cathode electrode toward the anode at the far side of the gel.

While the particular ELECTROPHORESIS RUNNING TANK ASSEMBLY is herein shown and described in detail, it is to be understood that the subject matter which is encompassed by the present invention is limited only by the claims.

What is claimed is:

1. Assembly for electrophoresis, comprising:
    at least one tank formed with a gel tray platform including a top surface configured for holding at least one gel tray containing gel;
    at least an anode reservoir on a first side of the gel tray platform and at least a cathode reservoir on a second side of the gel tray platform, both reservoirs configured for holding buffer during electrophoresis, the anode reservoir being larger than the cathode reservoir, both reservoirs having a respective closed bottom, a respective top opposed to the respective closed bottom, and a respective buffer chamber therebetween, the anode reservoir and the cathode reservoir extending laterally inward under the gel tray;

at least an anode in the anode reservoir and at least a cathode in the cathode reservoir, the anode and cathode being disposed in the respective buffer chamber and spaced above the respective closed bottom, a first distance being established between the anode and a side of the gel tray facing the anode and at least a second distance being established between the cathode and a side of the gel tray facing the cathode, the first distance being greater than the second distance;

at least a first source of illumination facing the platform;

at least a second source of illumination facing the platform and facing the first source of illumination with the platform between the first and second sources of illumination, the first and second sources of illumination positioned to emit light along respective first and second central light axes that are coplanar with each other and that are parallel to and spaced from the top surface of the gel tray platform, the top of the gel tray platform being a horizontal top on top of which is located a shelf platform with a top surface that is at least partially speculative and opaque and configured for receiving the gel tray thereon.

2. The assembly of claim 1, comprising:
at least a first lens positioned between the first source of illumination and the platform to focus light from the first source of illumination in a pattern defining a first central light axis; and
at least a second lens positioned between the second source of illumination and the platform to focus light from the second source of illumination in a pattern defining a second central light axis.

3. The assembly of claim 1, wherein the anode and cathode are made of carbon.

4. The assembly of claim 1, wherein the anode and cathode are elongated and define respective longitudinal axes parallel to the closed bottoms of the respective buffer chambers.

5. The assembly of claim 2, wherein the first lens is an elongated horizontally-oriented cylindrical lens.

6. The assembly of claim 2, wherein the first source of illumination is recessed radially outward of a surface with which the first lens is mounted.

7. The assembly of claim 1, wherein the first source of illumination has a flat distal end through which light emerges.

8. The assembly of claim 1, wherein the first and second sources of illumination face each other.

9. The assembly of claim 1, wherein at least the cathode is laterally spaced from the gel tray by a distance less than three millimeters.

10. Assembly for electrophoresis, comprising:
at least one tank holding a gel tray platform assembly including a top surface configured for holding at least one gel tray containing gel with DNA therein;
at least a first light emitting diode (LED) juxtaposed with a first wall of the tank, the first wall facing the platform;
at least a second LED juxtaposed with a second wall of the tank, the second wall facing the platform;
at least a first optical element positioned between the first LED and the platform to pass light from the first LED to the gel tray platform;
a gel tray with a clear bottom wall defining a bottom surface, the bottom wall supporting a gel defining a top gel surface, the gel tray being positioned on the top surface of the gel tray platform assembly, respective first and second light axes from the respective first and second LEDs being coplanar with a plane midway between the top surface of the gel and the bottom surface of the gel tray, the top surface of the gel tray platform assembly being at least partially speculative and opaque.

11. The assembly for electrophoresis of claim 10, comprising a filter removably engageable with the tank to filter light from the LED from an observer of the gel while allowing emitted wavelengths from the stain to pass through to the observer, the filter having a top of opaque filter material with a central transparent or translucent colored window, the top being parallel to the top surface of the gel tray platform assembly.

12. The assembly for electrophoresis of claim 10, comprising:
at least a second lens positioned between the second LED and the gel tray platform assembly to focus light from the second LED along the light axis.

13. The assembly for electrophoresis of claim 10, comprising:
at least an anode reservoir on a first side of the gel tray platform assembly and at least a cathode reservoir on a second side of the gel tray platform assembly, both reservoirs configured for holding buffer during electrophoresis;
at least an anode in the anode reservoir and at least a cathode in the cathode reservoir, a first distance being established between the anode and a side of the gel tray facing the anode when the gel tray is positioned on the gel tray platform assembly and at least a second distance being established between the cathode and a side of the gel tray facing the cathode when the gel tray is positioned on the gel tray platform assembly.

14. The assembly for electrophoresis of claim 13, wherein the first distance is greater than the second distance.

15. The assembly for electrophoresis of claim 13, wherein the anode reservoir is larger than the cathode reservoir.

16. The assembly for electrophoresis of claim 10, wherein the optical element is a first lens and first LED is one of a first group of LEDs oriented in a horizontal row and recessed below a surface onto which the first lens is mounted and the second LED is one of a second group of LEDs oriented in a horizontal row and recessed below a surface onto which the second lens is mounted.

17. The assembly for electrophoresis of claim 16, wherein the first and second groups of LEDs face each other.

18. Assembly for electrophoresis for allowing an operator to observe the progress of DNA bands as they migrate and separate comprising:
at least a first reservoir for buffer with a cathode element therein;
at least a second reservoir for buffer with an anode element therein;
the cathode element and anode element being configured for connection to at least one source of voltage;
at least one gel tray platform between the elements and configured for supporting at least one gel tray containing a gel having DNA therein;
at least a first source of illumination juxtaposed with a first side of the gel tray platform and positioned to emit light along a light axis, the gel tray platform having a horizontal top on top of which is located a shelf platform with a top surface that is at least partially speculative and opaque, the gel tray resting on the shelf platform and at least a second source of illumination juxtaposed with a second side of the gel tray platform, the second side of the gel tray platform not being the first side of the gel tray platform.

19. The assembly of claim 18, wherein the cathode element is positioned near a proximate edge of the gel and the anode element is positioned near a distal edge of the gel that is opposite to the proximal edge.

20. The assembly of claim 18, wherein, the light axis is co-planar with a plane that is midway between a top surface of the gel and a bottom surface of the gel tray.

21. The assembly of claim 18, wherein the light axis is orthogonal to a line intersecting the anode and cathode.

22. The assembly of claim 18, wherein the gel tray is made of clear plastic such that a bottom of the gel tray in cooperation with the top surface of the gel shelf platfo establishes a light pipe to excite the stain associated with the DNA.

23. The assembly of claim 18, wherein the first source of illumination comprises a blue light emitting diode (LED) and the gel comprises a green stain.

24. The assembly of claim 18, comprising a lens positioned between the first source of illumination and the gel platform and located to focus light from the first source of illumination on a first edge of the gel.

25. The assembly of claim 18, comprising an opening in a wall of the assembly between the first source of illumination and the gel platform and a lens extending inwardly past the opening and located to focus light from the first the source of illumination on a first edge of the gel, the lens being coupled to a transparent block disposed in the opening to at least partially seal the first source of illumination from fluid in the first reservoir.

26. The assembly of claim 18, comprising a filter configured to filter light from the at least one source of illumination from an observer of the gel while allowing emitted wavelengths from the stain to pass through to the observer.

27. The assembly of claim 26, wherein the filter is established by a hood with a top of filter material for mounting a camera.

28. The assembly of claim 27, wherein at least one side of the hood is formed with filter material to allow observation simultaneously while running the gel.

* * * * *